United States Patent [19]

Bovy et al.

[11] Patent Number: 5,872,122
[45] Date of Patent: Feb. 16, 1999

[54] PYRIMIDINYLAMIDINO β-AMINO ACID DERIVATIVES USEFUL AS INHIBITORS OF PLATELET AGGREGATION

[75] Inventors: Philippe R. Bovy, Mareil Marly, France; Henry E. Dayringer, Chesterfield, Mo.; Steven P. Adams, Andover, Mass.

[73] Assignee: Monsanto Company, St. Louis, Mo.

[21] Appl. No.: 951,560

[22] Filed: Oct. 16, 1997

[51] Int. Cl.⁶ .................. A61K 31/505; A61K 38/06; C07D 239/26; C07K 5/08
[52] U.S. Cl. .................. 514/256; 514/18; 514/20; 530/331; 544/333; 544/335
[58] Field of Search ............... 514/18, 20, 256; 530/331; 544/333, 335

[56] References Cited

U.S. PATENT DOCUMENTS

| | | | |
|---|---|---|---|
| 3,994,976 | 11/1976 | Bockstahler | 260/564 R |
| 4,052,455 | 10/1977 | Matier et al. | 260/562 R |
| 4,096,183 | 6/1978 | Matier et al. | 260/556 AR |
| 4,130,663 | 12/1978 | Matier et al. | 424/326 |
| 4,169,106 | 9/1979 | Diamond et al. | 260/558 A |
| 4,206,142 | 6/1980 | Matier et al. | 260/556 AR |
| 4,259,482 | 3/1981 | Matier et al. | 544/8 |
| 4,517,686 | 5/1985 | Ruoslahti et al. | 514/12 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,791,102 | 12/1988 | Bernat et al. | 514/19 |
| 4,879,313 | 11/1989 | Tjoeng et al. | 514/616 |
| 4,977,168 | 12/1990 | Bernat et al. | 514/330 |
| 4,997,667 | 3/1991 | Nofre et al. | 426/548 |
| 5,039,805 | 8/1991 | Alig et al. | 546/224 |
| 5,053,393 | 10/1991 | Tjoeng et al. | 514/18 |
| 5,100,875 | 3/1992 | Marguerie de Rotrou | 514/18 |
| 5,104,876 | 4/1992 | Piwinski et al. | 514/254 |
| 5,220,050 | 6/1993 | Bovy et al. | 514/357 |
| 5,256,812 | 10/1993 | Alig et al. | 560/35 |
| 5,270,319 | 12/1993 | Belliotti et al. | 514/269 |
| 5,344,957 | 9/1994 | Bovy et al. | 560/35 |
| 5,430,024 | 7/1995 | Alig et al. | 514/18 |
| 5,455,348 | 10/1995 | Austel et al. | 544/238 |
| 5,597,825 | 1/1997 | Himmelsbach et al. | 514/255 |

FOREIGN PATENT DOCUMENTS

| | | |
|---|---|---|
| 0275748 | 7/1988 | European Pat. Off. . |
| 0298820 | 1/1989 | European Pat. Off. . |
| 0372486 | 6/1990 | European Pat. Off. . |
| 0381033 | 8/1990 | European Pat. Off. . |
| 0445796 | 9/1991 | European Pat. Off. . |
| 0496378 | 7/1992 | European Pat. Off. . |
| 0502536 | 9/1992 | European Pat. Off. . |
| 0513810 | 11/1992 | European Pat. Off. . |
| 0528369 | 2/1993 | European Pat. Off. . |
| 0539343 | 4/1993 | European Pat. Off. . |
| 0542708 | 5/1993 | European Pat. Off. . |
| 2006760 | 5/1979 | United Kingdom . |
| WO 9307867 | 4/1993 | WIPO . |
| WO 9312074 | 6/1993 | WIPO . |
| WO 9312103 | 6/1993 | WIPO . |
| WO 9316036 | 8/1993 | WIPO . |
| WO 9318058 | 9/1993 | WIPO . |
| WO 9400424 | 1/1994 | WIPO . |
| WO 9422820 | 10/1994 | WIPO . |
| WO 9506038 | 3/1995 | WIPO . |

OTHER PUBLICATIONS

Ginsberg, M. et al. "J. Biol. Chem." 260(7), 3931–36 (1985).
Haverstick, D. et al. "Blood" 66(4), 946–952 (1985).
Kloczewiak, M. et al. "Biochemistry" 23, 1767–1774 (1984).
Plow, E.F. et al. "PNAS" (USA) 82, 8057–8061 (1985).
Ruggeri, Z.M. et al. "PNAS" (USA) 83, 5708–5712 (1986).
Ruoslahti, E. & Pierschbacher, M.D. "Science" 238, 491–497 (1987).
Zablocki, J.A. et al. "Exp. Opin Invest. Drugs" 3(5), 437–448 (1994).
Zablocki, J.A. et al. "J. Med. Chem." 38, 2378–2394, (1995).
Dialog File 351 "Derwent WPI" Acc. No. 89–009875/198902, 1989.
Dialog File 351 "Derwent WPI" Acc. No. 93–272776/199334, 1993.

*Primary Examiner*—Yogendra N. Gupta
*Attorney, Agent, or Firm*—Fitzpatrick, Cella, Harper & Scinto

[57] ABSTRACT

This invention provides a compound of the formula

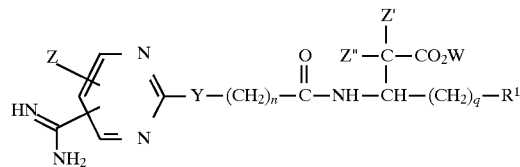

or a pharmaceutically acceptable salt thereof. The invention also provides pharmaceutical compositions of such compounds and a method of treatment to inhibit aggregation of platelets.

14 Claims, No Drawings

PYRIMIDINYLAMIDINO β-AMINO ACID DERIVATIVES USEFUL AS INHIBITORS OF PLATELET AGGREGATION

BACKGROUND OF THE INVENTION

1. Field of the Invention

This invention is directed to novel pyrimidinylamidino β-amino acid compounds which inhibit aggregation of platelets. This invention is also directed to a pharmaceutical composition comprising these compounds. This invention is further directed to a method for inhibiting platelet aggregation.

2. Related Background Art

Platelets are cellular components of the blood responsible for coagulation and clot formation. Fibrinogen is a glycoprotein which binds to platelets in the blood coagulation mechanism. When a blood vessel receives an injury, platelets initially form a monolayer adhering to collagen in the underlying subendothelial matrix. The adherence of the platelets leads to their activation according to a process in which receptors for gpIIb-IIa (a membrane glycoprotein) undergo a conformational change to allow for fibrinogen binding. The platelets then bind fibrinogen, which then adheres to additional platelets, forming a thrombus. At the same time, factor Xa mediates the cleavage of prothrombin to thrombin. Thrombin cleaves fibrinogen to fibrin, which forms a stable clot. Naturally occurring plasmin eventually cleaves fibrin and dissolves the clot. Inhibitors of different steps in this pathway are effective in modulating or preventing thrombus formation and/or clotting.

It is also known that fibronectin, a large glycoprotein and a major extracellular matrix protein, interacts with fibrinogen and fibrin, as well as with other structural molecules such as actin, collagen, and proteoglycans. It has been found that relatively large peptide fragments found in fibronectin's cell-binding domain have cell-binding activity. See U.S. Pat. Nos. 4,517,686; 4,589,881; and 4,661,111. Additionally, short peptide fragments of the same molecule have been found to have cell-binding activity, or activity inhibiting cell-binding when placed in solution or suspension, presumably because they bind to the cell and prevent its binding to the substrate. See U.S. Pat. Nos. 4,578,079 and 4,614,517. Other synthetic peptides have also been used to inhibit binding of fibrinogen to platelets. See, e.g., Koczewiak et al., Biochem., 23, 1767–1774 (1984); Plow et al., Proc. Nat'l Acad. Sci., 82, 8057–8061 (1985); Ruggeri et al., Proc. Nat'l Acad. Sci., 83, 5708–5712 (1986); Ginsberg et al., J. Biol. Chem., 260, 3931–3936 (1985); Haverstick et al., Blood, 66, 946–952 (1985); Ruoslahti and Pierschbacher, Science, 238, 491–497 (1987); U.S. Pat. Nos. 5,053,393 and 5,344,957; European Pat. App. 275,748; and European Pat. App. 298,820.

Compounds containing an amidino group attached to an aromatic ring are also known to have cell-binding activity.

European Patent Application 496,378 discloses amidino-biphenyl compounds which inhibit cell-cell and cell-matrix interaction and are thus useful for treating thrombosis, cerebrovascular diseases, pulmonary embolisms, myocardial infarction, arteriosclerosis, osteoporosis, and tumor metastases. European Patent Application 445,796 discloses amidino-substituted acetic acid derivatives which have inhibitory action on the bonding of adhesive proteins to platelets as well as on platelet aggregation and cell-cell adhesion.

European Patent Application 372,486 discloses N-acyl β-amino acid derivatives and their salts. These compounds are said to be useful for inhibiting platelet aggregation in the treatment of thrombosis, stroke, myocardial infarction, inflammation, arteriosclerosis, and metastasis.

European Patent Application 381,033 discloses amidinoaryl or guanidinoaryl substituted alkanoic acid derivatives useful for the treatment of thrombosis, apoplexy, cardiac infarction, inflammation, arteriosclerosis, and tumors.

PCT Application WO 95/06038 discloses cyclic ureas substituted by an amidinophenyl group and a β-amino acid. These compounds are useful as platelet aggregation inhibitors.

PCT Applications WO 93/18058 and WO 95/06038, and European Patent Applications EP 542,708 and EP 539,343 disclose amidinobenzenaminosuccinyl acid derivatives useful as platelet aggregation inhibitors.

PCT Applications WO 94/00424, WO 93/12074 and WO 93/12103 disclose phenylamidine alkanoic acids and lactones useful as platelet aggregation inhibitors.

PCT Application WO 94/22820 discloses amidinophenyl pyrrolidinones, piperidinones, and azetidinones useful as platelet aggregation inhibitors.

U.S. Pat. Nos. 5,220,050 and 5,344,957 disclose amidinophenyl-substituted β-amino acid derivatives which are useful as platelet aggregation inhibitors.

J. A. Zablocki et al., J. Med. Chem., 38, 2378–2394 (1995) and European Patent Application No. 502,536, disclose aminobenzamidino succinyl compounds which are useful as platelet aggregation inhibitors.

The present invention is directed to novel pyrimidinylamidino β-amino acid compounds which inhibit platelet aggregation.

SUMMARY OF THE INVENTION

In accordance with the present invention, novel substituted pyrimidinylamidino β-amino acids are provided which modulate and/or inhibit platelet aggregation. These compounds are represented by the general formula (I):

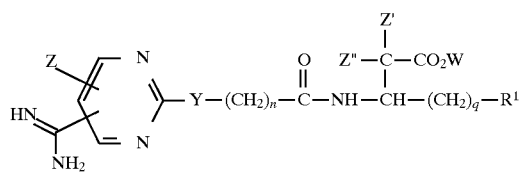

or a pharmaceutically acceptable salt thereof, wherein

Z, Z', and Z" are independently halo, alkoxy, alkyl, hydrogen or hydroxy;

Y is methylene, alkenyl having 2 to 4 carbon atoms, alkynyl having 2 to 4 carbon atoms or carbonyl;

n is an integer from 1 to 6;

W is hydrogen, alkyl, methoxyalkyl or aralkyl;

q is an integer from 0 to 3; and $R^1$ is hydrogen; alkyl; cycloalkyl; alkoxy; alkylthio; alkylsulfonyl; aryl; aralkyl; heterocyclic; or

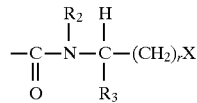

wherein $R^2$ is hydrogen, alkyl, aryl, or aralkyl;

$R^3$ is hydrogen, alkyl, aryl, or aralkyl;

r is an integer from 0 to 2; and

X is CN, $CO_2R^4$, $CONH_2$, $CONHR^4$ or $CON(R^4)_2$; wherein $R^4$ is hydrogen, alkyl, aryl, or aralkyl.

This invention is also directed to a novel pharmaceutical composition comprising compounds of the formula I useful in inhibiting or modulating platelet aggregation or the like, particularly in inhibiting or modulating platelet aggregation by administrating an amount between 0.5 mg/kg to 10 mg/kg, preferably 3 mg/kg, to an animal in need thereof.

This invention is further directed to a method to therapeutically inhibit or modulate platelet aggregation or the like in a mammal in need of such treatment comprising a compound of the formula I in unit dosage form.

Many other objects and purposes of the invention will be clear from the following detailed description of the invention.

DETAILED DESCRIPTION OF THE INVENTION

The following terms used herein to describe substituent groups are defined as follows. The term "alkyl" refers to a straight or branched alkyl group containing from 1 to 8 carbon atoms. The term "alkenyl" refers to a straight or branched hydrocarbon group containing from 1 to 8 carbon atoms and at least one carbon-carbon double bond. The term "alkynyl" refers to a straight or branched hydrocarbon group containing from 1 to 8 carbon atoms and at least one carbon-carbon triple bond. The term "cycloalkyl" refers to a cyclic alkyl group containing up to 8 carbon atoms. The term "aryl" refers to a group derived from a cyclic aromatic compound having up to 12 carbon atoms and which may be unsubstituted or substituted by alkyl, halo, alkoxy, trifluoromethyl, hydroxy, nitro, cyano, amino, dialkylamino or carboxyl groups. The term "aralkyl" refers to an alkyl substituent substituted by an aryl group. The term "heterocyclic" refers to a group derived from a monocyclic or fused bicyclic compound having no more than 10 ring atoms among which are from 1 to 4 atoms selected from nitrogen, oxygen and sulfur, and which may be unsubstituted or substituted by alkyl, halo, alkoxy, cyano, hydroxy, nitro, trifluoromethyl, amino, dialkylamino or carboxyl groups. The term "halo" refers to the substituent formed by covalent attachment of fluorine, chlorine, bromine, or iodine. The term "DMF" refers to N,N-dimethylformamide.

The term "pharmaceutically acceptable salt" refers to a salt resulting from contact between a compound of this invention and an acid or base whose counter-ion is generally considered suitable for human consumption. A pharmaceutically acceptable salt comprises an ion derived from a compound of this invention, together with a counter-ion derived from an acid or base. Pharmaceutically acceptable salts derived from acids include such counter-ions as, for example, chloride, bromide, iodide, sulfate, phosphate, acetate, propionate, lactate, maleate, oxalate, malate, succinate, tartrate, and citrate. All of these salts may be prepared by conventional means by reacting, for example, the corresponding acid with a compound of this invention. Pharmaceutically acceptable salts derived from bases include such counter-ions as, for example, aluminum, calcium, lithium, magnesium, potassium, sodium, zinc, and organic cations derived from N,N'-dibenzylethylenediamine, chloroprocaine, choline, diethanolamine, ethylenediamine, meglumine (N-methylglucamine), and procaine.

A compound of the present invention has the following general formula (I):

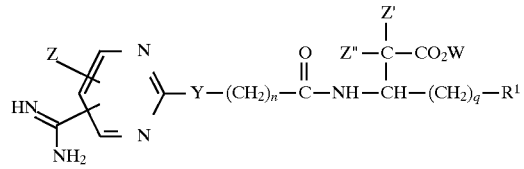

or a pharmaceutically acceptable salt thereof, wherein

Z, Z', and Z" are independently halo, alkoxy, alkyl, hydrogen or hydroxy;

Y is methylene, alkenyl having 2 to 4 carbon atoms, alkynyl having 2 to 4 carbon atoms or carbonyl;

n is an integer from 1 to 6;

W is hydrogen, alkyl, methoxyalkyl or aralkyl;

q is an integer from 0 to 3; and $R^1$ is hydrogen; alkyl; cycloalkyl; alkoxy; alkylthio; alkylsulfonyl; aryl; aralkyl; heterocyclic; or

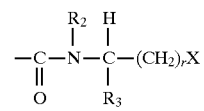

wherein $R^2$ is hydrogen, alkyl, aryl, or aralkyl;

$R^3$ is hydrogen, alkyl, aryl, or aralkyl;

r is an integer from 0 to 2; and

X is CN, $CO_2R^4$, $CONH_2$, $CONHR^4$ or $CON(R^4)_2$; wherein $R^4$ is hydrogen, alkyl, aryl, or aralkyl.

A preferred embodiment of the present invention is a compound of the general formula I, or a pharmaceutically acceptable salt thereof, wherein Z, Z', and Z" are hydrogen. Another preferred embodiment of the present invention is a compound of the general formula I, or a pharmaceutically acceptable salt thereof, wherein Z, Z', and Z" are hydrogen; q is 0, and Y is methylene. Another preferred embodiment of the present invention is a compound of the general formula I, or a pharmaceutically acceptable salt thereof, wherein Z, Z', and Z" are hydrogen; q is 0, and Y is methylene; n is 3, and $R^2$ is hydrogen. Another preferred embodiment of the present invention is a compound of the general formula I, or a pharmaceutically acceptable salt thereof, wherein Z, Z', and Z" are hydrogen; q is 0, and Y is methylene; n is 3, and $R^2$ is hydrogen; and r is 0.

The compounds of this invention are useful in inhibiting platelet aggregation, for example, in treatment of thrombosis, stroke, myocardial infarction, inflammation, arteriosclerosis, and metastasis.

As previously noted, the compositions of this invention may be employed in a pharmaceutical composition for inhibiting or modulating platelet aggregation. In addition, this invention is also directed to a method of therapeutically inhibiting or modulating platelet aggregation in an animal in need thereof by administering thereto a unit dosage amount of the compounds of this invention.

The total daily dose of the compounds of this invention administered to a host in single or divided doses may be in amounts, for example, from 0.001 to 100 mg/kg body weight daily and more usually 0.01 to 10 mg/kg. Dosage Unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diets, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants and vehicles as desired.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic monoglycerides or diglycerides. In addition, fatty acids such as oleic acid find use in injectable preparations.

Suppositories for rectal administration of the drug can be prepared by mixing the drug with a suitable nonirritating excipient such as cocoa butter and polyethylene glycols which are solid at ordinary temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants such as wetting agents emulsifying and suspending agents, and sweetening, flavoring, and perfuming agents.

While the compounds of the invention can be administered as the sole active pharmaceutical agent, they can also be used in combination with one or more active pharmaceutical agents. When administered as a combination, the therapeutic agents can be formulated as separate compositions which are given at the same time or different times, or the therapeutic agents can be given as a single composition.

In the structures and formulas herein, the bond drawn across a bond of an aromatic ring can be to any available atom on the aromatic ring.

The compounds in this invention can exist in various isomeric forms and all such isomeric forms are meant to be included. Tautomeric forms are also included in the invention. Pharmaceutically acceptable salts of such isomers and tautomers are meant to be included as well.

It is also contemplated that β-amino acids ($H_2N$—CHR—$CH_2$—$CO_2H$) used in this invention may be replaced by homo β-amino acids ($H_2N$—$CH_2$—CHR—$CO_2H$).

The compounds listed above may be prepared by standard synthetic methods combined with methods analogous to solution phase peptide synthesis (see: The Peptides: Analysis, Synthesis, Biology (E. Gross and J. Meienhofer, eds.), Vol. 1–5, Academic Press;, New York)), the disclosure of which is hereby incorporated by reference.

Eight general synthetic sequences which outline preferred methods for preparation of the compounds of this invention are outlined in the following Schemes I–VIII.

Scheme I describes a general synthesis of 5-cyano-2-pyrimidinealkanoic acids, which can be applied to synthesize pyrimidine alkanoic acids of various lengths. The pyrimidine ring is built by condensation of 2-cyano-3-(dimethylamino)acrolein with an amidine derivative in the presence of a base. A great variety of bases may be used to effect this transformation. A particularly preferred base is triethylamine ($NEt_3$).

SCHEME I

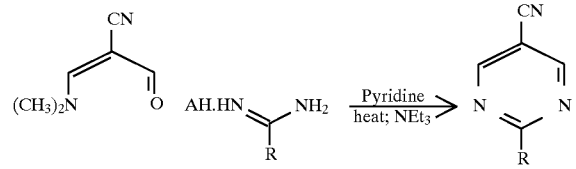

In this scheme, "R" is an alkoxycarbonyl-substituted alkyl chain, which may contain a carbonyl group or an unsaturated bond. "A" is a counterion from an acid HA.

The 2-cyano-3-(dimethylamino)acrolein may be prepared by a procedure similar to that described by C. Reichart et al. in Angew. Chem. Internat'l Ed., 11, 62, 1972. The amidine-acid is typically prepared from the corresponding cyano acid by the Pinner synthesis.

Scheme II provides a detailed description of the synthesis of 5-cyano-2-pyrimidinepentanoic acid.

SCHEME II

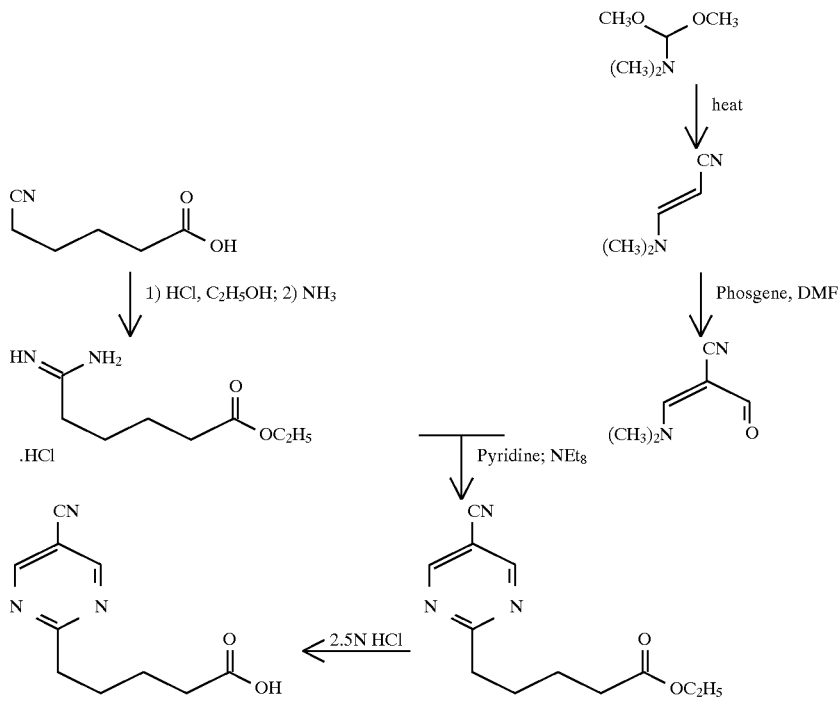

The amidine and the 2-cyano-3-(dimethylamino)acrolein are typically condensed in a mixture of pyridine and triethylamine ($NEt_3$) at a temperature between 20° C. and reflux temperature of the solvent mixture to produce the 5-cyanopyrimidine ester in good yield. This ester can be hydrolyzed to the acid with dilute aqueous acid (e.g. 2.5N hydrochloric acid).

Scheme III describes a route to cyanopyrimidines that relies on building the pyrimidine ring by reacting mucobromic acid with an amidine derivative similar to that described in Scheme I. This method provides a 5-bromopyrimidine derivative as described by G. Kosolapoff and C. H. Roy, J. Org. Chem., 26, 1895, 1961. The bromine substituent can be exchanged for a nitrile group by refluxing the bromopyrimidine in quinoline in the presence of CuCN as reported by A. E. Frissen et al., Tetrahedron, 45, 5611–5620, 1989.

SCHEME III

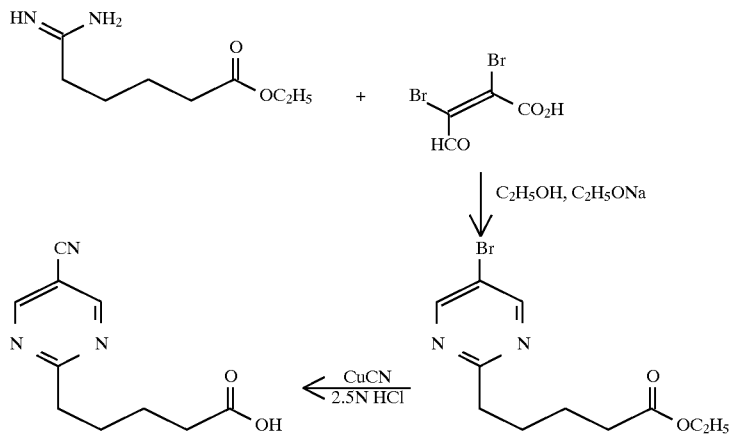

Scheme IV describes alternative routes to 5-cyano-2-pyrimidinepentanoic acid. A halopyrimidinonitrile is coupled to an alkanoic acid derivative using a palladium (0) based coupling reaction ["Heck Reaction"—Palladium Reagents in Organic Syntheses (Richard F. Heck), Academic Press, New York, 1985]. The preferred conditions for the coupling of an iodoalkanoic acid derivative have been described by T. Sakamoto et al. in Synthesis, 485, 1988.

SCHEME IV

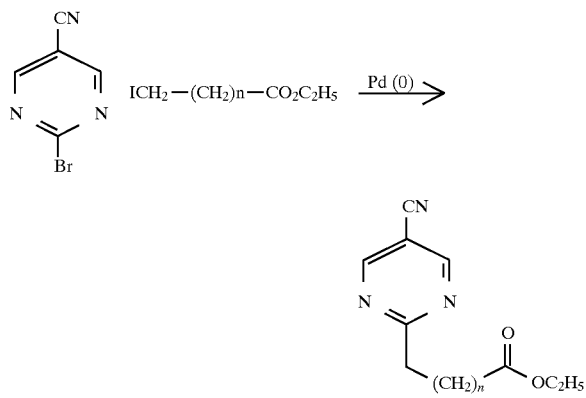

The preferred conditions for the palladium coupling reaction generally differ if an iodoalkynoic acid or an iodoalkenoic acid starting material is used in place of the iodoalkanoic acid. For an iodoalkynoic acid starting material, tetrakis(triphenylphosphine)-palladium(0) is used as the coupling catalyst and piperidine as the solvent (for related conditions see: H. A. Dieck and F. R. Heck, J. Organometallic Chem., 259–263 (1975)). For an iodoalkenoic acid starting material, the phase transfer conditions of Jeffery and Larock are employed (T. Jeffery, J. Chem. Soc. Chem. Commun. 1287–89 (1984); R. C. Larock Tetrahedron Lett. 2603–2606 (1989)). These conditions comprise use of a tetrabutylammonium salt as a phase transfer agent, palladium (II) acetate as a coupling catalyst, potassium acetate as a base, and N,N-dimethylformamide (DMF) as a solvent. These are extremely mild conditions which afford a good yield of coupled compound. The required omega iodo acids are commercially available or can be synthesized by iodination of corresponding alcohols.

In Scheme V is described an alternative method for the preparation of a (cyanopyrimidinyl)alkenoic acid using a standard Wittig Reaction (B. E. Maryanoff, A. Reitz, Chem. Rev. 863–927 (1989)) between 5-cyano-2-formyl-pyrimidine and an omega-substituted (carboxyalkyl) triphenylphosphonium bromide (for related conditions see: J. Am. Chem. Soc., 397 (1970); ibid., 6831 and 7185 (1973)).

SCHEME V

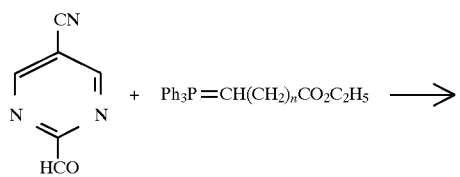

-continued
SCHEME V

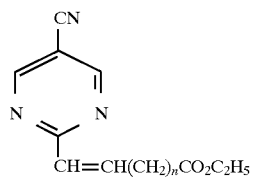

The following are examples of procedures for preparation of compounds of Formula I where Z is different from hydrogen. The substituents Z, Z' and Z" (where Z, Z' and Z" may be halo, alkyl, hydroxy, or alkoxy) can be present in the starting pyrimidine or pyrimidine precursor or introduced at a latter stage. Introduction of fluorine on the ring is best performed at the expense of the corresponding amino derivative, using diazotization followed by dediazonation in the presence of a fluoride-containing counter-ion (D. E. Rosenberg et al., Tet. Lett., 21, 4141–4, 1980; Scheme 3a). Other modifications of this method can also be useful (Rosenfeld and Widdowson, J. Chem. Soc. Chem. Comm. 914, 1979). An alkyl group can be introduced by low temperature lithium halogen exchange followed by quenching with the appropriate aldehyde (see: W. E. Parham, C. K. Bradsher, Acct. Chem. Res. 300 (1982)). The resultant alcohol is then converted to the alkyl group by hydrogenolysis (Reductions in Organic Chemistry (M. Hudlicky, ed.), John Wiley & Sons, New York, 1984).

Scheme VI describes the coupling of a 5-cyanopyrimidinealkanoic acid to a tert-butyl ester (tBut) of a beta amino acid and the conversion of the cyano group into the amidine group via the addition of ammonia in solution in a dry solvent, preferably methanol. Thus, compounds of formula I can be obtained by coupling an appropriately protected beta amino acid derivative (a tert-butyl ester is preferred) with the acid obtained as described in Schemes I–V. The first step in Scheme VI describes the coupling using an activated form of the acid. Suitable activated forms include anhydrides, internal anhydrides, acid chlorides and the various activated forms described in Principles of Peptide Synthesis, Bodansky, 1984, Springer-Verlag. Preferentially, the amide bonds are formed using standard coupling reagents, e.g. dicyclohexylcarbodiimide (DCC), carbonyldiimidazole, disuccinimidyl carbonate (DSC), benzotriazole-1-yl-oxy-tris-(dimethylamino)-phosphonium hexafluorophosphate (BOP) or isobutyl chloroformate (i-BCF) in combination with a base, for example N-methylmorpholine (NMM) (mixed anhydride method). After formation of the amide bond, the resulting cyanoester can be reacted with ammonia in dry methanol to give the amidine derivative. The tert-butyl ester is deprotected by well known methods, e.g., trifluoroacetic acid (TFA) or hydrobromic acid in acetic acid. When an ester sensitive to nucleophilic displacement (e.g., ethyl or methyl) is used, it is advantageous to hydrolyze the ester first by gentle acidic hydrolysis and to react the cyano acid with ammonia.

SCHEME VI
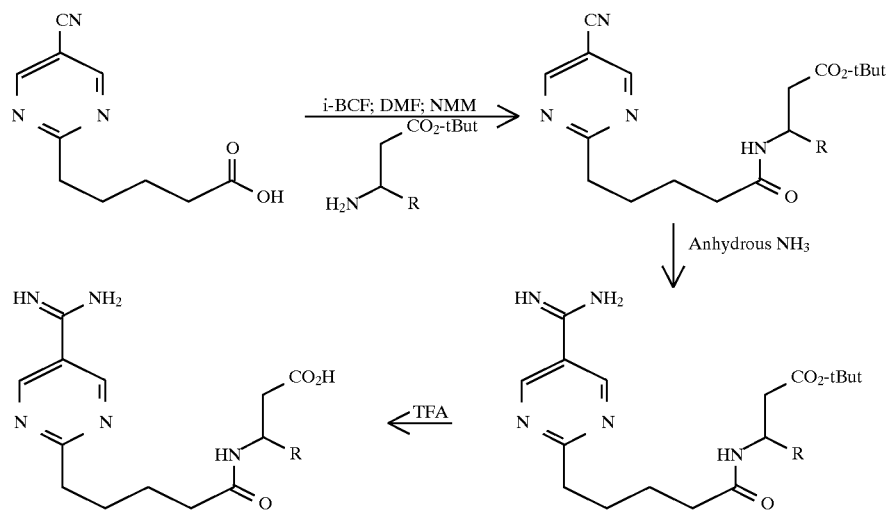
In this scheme, "R" represents —(CH)$_q$R$^1$— in Formula I.
Scheme VII describes several general routes for preparation of beta amino acids which are in turn used to prepare the compounds of Formula I. This scheme illustrates a general method for preparation of aromatic amino acids.
SCHEME VII
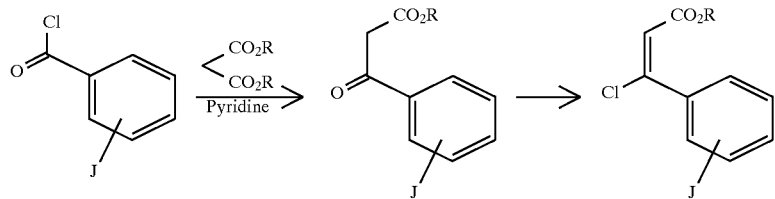

-continued
SCHEME VII

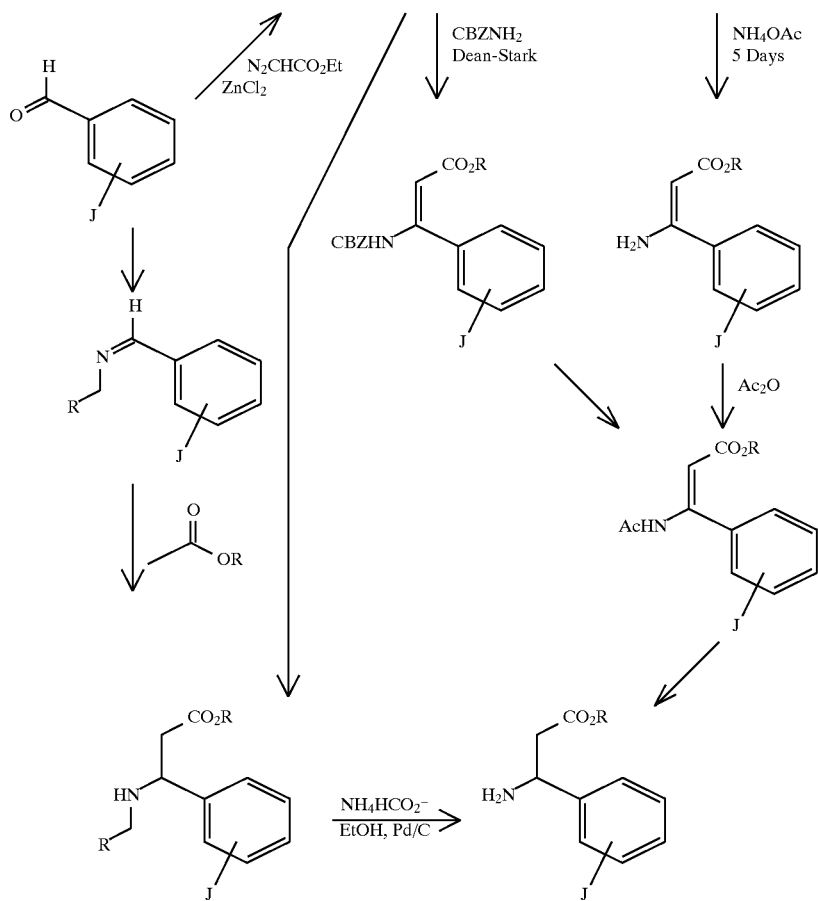

In this scheme, "J" represents one or more alkyl, halo, alkoxy, trifluoromethyl, hydroxy, nitro, cyano, amino, dialkylamino, or carboxyl groups.

Scheme VIII describes the coupling of a 5-cyanopyrimidinealkanoic acid to a peptide derivative and the conversion of the cyano group into an amidine group via the addition of ammonia in solution in a dry solvent, preferably methanol.

SCHEME VIII

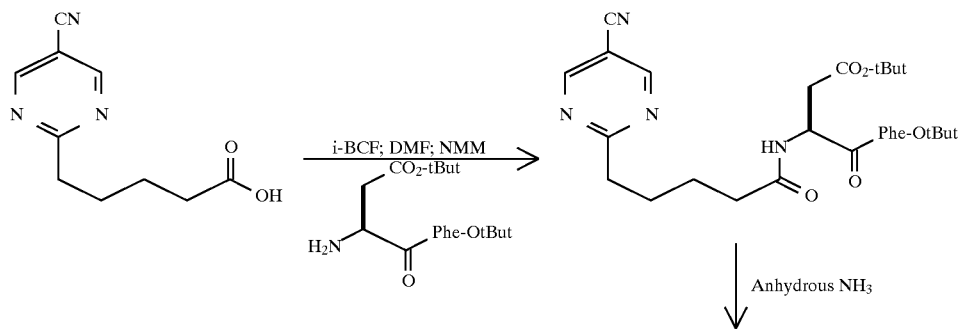

-continued
SCHEME VIII

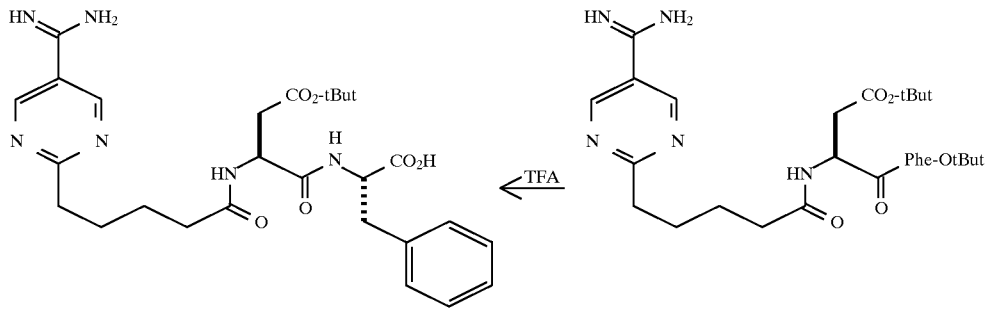

Purification of final compounds is typically accomplished by means of reverse phase high pressure liquid chromatography as described, for example, in High Performance Liquid Chromatography Protein and Peptide Chemistry, F. Lottspeich, A. Henscher, K. P. Hupe, eds. (Walter DeGruyter, New York, 1981), or by crystallization.

The following examples are intended as illustrations of certain preferred embodiments of the invention, and no limitation of the invention is implied.

EXAMPLE 1

[S,(R*,R*)]-3-[[5-[5-(aminoiminomethyl)-2-pyrimidinyl]-1-oxopentyl]amino]-4-[[2-amino-2-oxo-1-(phenylmethyl)ethyl]amino]-4-oxobutanoic acid

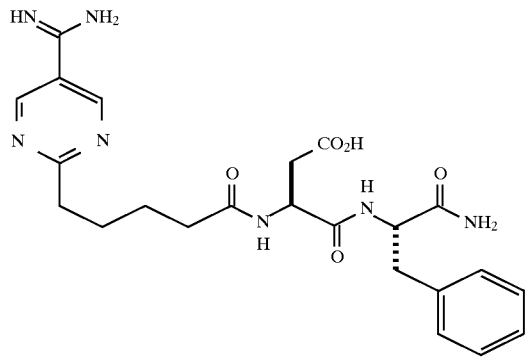

Step 1. Preparation of ethyl 6-amino-6-imino-hexanoate hydrochloride

A mixture of 28 g methyl 5-cyanovalerate, 20 mL ethanol and 100 mL of 4N HCl in dioxane were mixed in a flask under a dry nitrogen atmosphere. The resulting solution was stirred at 4° C. for 36 hr in the stoppered flask. Diethyl ether (1 L) was added to the mixture and the mixture concentrated under a flow of nitrogen until an oily residue was obtained. The residue was triturated with 1 L of hexane and the supernatant liquid was decanted. The hexane trituration procedure was repeated twice until a waxy solid was obtained which was rapidly isolated by filtration under nitrogen. A solution of ammonia in methanol was added until the reaction mixture was basic and the resulting mixture was stirred at room temperature for 36 hr. The reaction mixture was concentrated in vacuo to a thick oil: $^1$H NMR (DMSO-d6) δ 1.2 (t, J=7.5 Hz, 3H); 1.6 (m, 4H); 2.4 (m, 4H); 4.05 (q, J =7.5 Hz, 2H); 8.8 (bs, 2H); 9.1 (bs, 2H); MS (M+H+ for $C_8H_{16}N_2O_2$) 173.1.

This material usually contained various quantities (up to 30%) of the corresponding methyl ester. No attempts were made to separate the two esters and the mixture was used as such in the next step.

Step 2. Preparation of ethyl 5-cyano-2-pyrimidine-pentanoate

A mixture of the amidine from Step 1 (30 g), 15 g of 2-cyano-3-(N,N-dimethylamino)acrolein (C. Reichart and W. D. Kermer, Synthesis, 1970, 2, 538), 75 mL pyridine and 75 mL triethylamine was stirred at 80° C. for 5 hr. The reaction mixture was concentrated in vacuo and partitioned between diethyl ether and water (pH 4). Concentration of the dried diethyl ether phase provided 20 g of a brown oil, which was purified by silica gel chromatography (eluant hexane-:ethyl acetate, 1:1). The pyrimidine derivative was obtained as a 2:1 mixture of the methyl and ethyl esters (12 g): $^1$H NMR (DMSO-d6) δ 1.25 (t, J=7.5 Hz); 1.65 (m, 2H); 1.85 (m, 2H); 2.35 (m, 2H); 3.05 (m, 2H); 3.65 (s); 4.1 (q, J=7.5 Hz); 8.9 (s, 2H).

Step 3. Preparation of 5-cyano-2-pyrimidinepentanoic acid

The ester mixture from Step 2 was stirred at 25° C. with 50 mL 2N hydrochloric acid. After a 36 hr reaction period, a yellow precipitate had formed which was filtered, washed with some water to give a waxy material which was dried in vacuo to produce a yellow solid. The solid was collected by filtration and washed with some water to give a waxy material which was dried in vacuo to produce a yellow solid (7 g): mp 99.0° C.; $^1$H NMR (DMSO-d6) δ 1.54 (m, 2H); 1.77 (m, 2H); 2.25 (m, 2H); 2.97 (m, 2H); 9.2 (s, 2H); ME (ES, M+H+) 206; IR 2227 $cm^{-1}$.

Step 4. Preparation of [S,(R*,R*)]-3-[[5-[5-(aminoiminomethyl)-2-pyrimidinyl]-1-oxopentyl]amino]-4-[[2-amino-2-oxo-1-(phenylmethyl)ethyl]amino]-4-oxo-butanoic acid The acid from Step 3 (350 mg, 1.71 mmol) was mixed with 250 mg isobutyl chloroformate (1.83 mmol), 250 μL N-methyl-morpholine (NMM) in 5 mL dimethylformamide. After stirring 5 min at 25° C., 500 mg of aspartame (1.7 mmol) were added along with 150 μL NMM. The reaction mixture was stirred at 25° C. for 2 hr and concentrated in vacuo. The residue was purified by HPLC: 450 mg of pure nitrite was isolated. A portion of that material was dissolved in 10 mL of methanol saturated with ammonia. After stirring at 25° C. for 16 hr, the major product was purified by HPLC on a linear gradient of 5% to 70% acetonitrile in water (0.05% TFA) over 25 min. The title compound was isolated after lyophilization as a white solid (70 mg): $^1$H NMR (DMSO-d6) δ 1.5 (m, 2H); 1.77 (m, 2H); 2.1 (m, 2H); 2.2 (m, 1H); 2.65 (m, 1H); 2.80 (m, 2H); 3.0 (m, 3H); 4.35 (m, 1H); 4.5 (m, 1H); 7.2 (bm, 6H); 7.75 (d, J=8 Hz, 1H); 8.1 (d, J=8 Hz, 1H) 9.02 (s, 2H); 9.2 (be, 2H); 9.5 (bs, 2H); 12.3 (bs,1H); MS (M+H+) 483.

Elemental Analysis: Calcd for $C_{23}H_{29}N_7O_5 \cdot CF_3CO_2H \cdot H_2O$. C, 48.78; H, 5.23; N, 15.92; Found: C, 49.07; H, 4.97; N, 15.86.

EXAMPLE 2

N-[N-[5-[5-(aminoiminomethyl)-2-pyrimidinyl]-1-oxopentyl]-L-alpha-aspartyl-L-phenylalanine

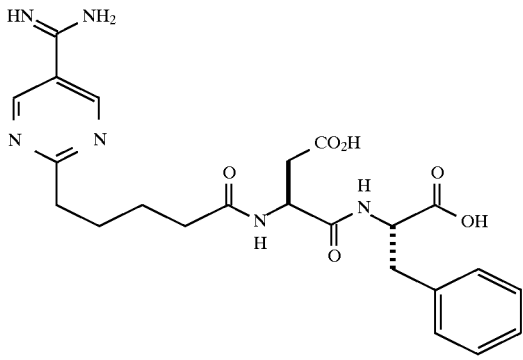

Step 1—Preparation of ethyl, N-[N-[5-[5-cyano-2-pyrimidinyl]-1-oxopentyl]-L-alpha-aspartyl-L-phenylalaninate The acid from Step 3, Example 1 (350 mg, 1.71 mmol) was mixed with 250 mg iso-butylchloroformate (1.83 mmol), 250 μL N-methyl-morpholine (NMM) in 5 mL dimethylformamide. After stirring 5 min at 25° C., 500 mg of aspartame (1.7 mmol) were added along with 150 μL NMM. The reaction mixture was stirred at 25° C. for 2 hr and concentrated in vacuo. The residue was purified by HPLC to give 450 mg of the title compound.

Step 2. Preparation of N-[N-[5-[5-(aminoiminomethyl)-2-pyrimidinyl]-1-oxopentyl]-L-alpha-aspartyl-L-phenylalanine A portion of the material (230 mg) isolated in Step 1 was stirred in 5 mL 0.5N HCl at 25° C. for 36 hr. The reaction mixture was lyophilized and to the dry residue, was added 10 mL of 3N ammonia in methanol. The reaction mixture was stirred at 30 hr at 25° C. A new peak was purified by HPLC and after lyophilization, a white powder (56 mg) was isolated: $^1$H NMR (DMSO-d6) δ 1.5 (m, 2H); 1.77 (m, 2H); 2.1 (m, 2H); 2.2 (m, 1H); 2.65 (m, 1H); 2.80 (m, 2H); 3.0 (m, 3H); 4.35 (m, 1H); 4.5 (m, 1H); 7.2 (bm, 6H); 7.75 (d, J=8 Hz 1H); 8.1 (d, J=8 Hz, 1H) 9.02 (s, 2H); 9.2 (bs, 2H); 12.3 (bs, 2H); MS (M+H+) 484.

Elemental Analysis: Calcd for $C_{23}H_{28}N_6O_6$1.33$CF_3CO_2H$.0.5$H_2O$. C, 47.77; H, 4.74; N, 13.03; Found: C, 47.70; H, 4.70; N, 13.02.

EXAMPLE 3

β-[[5-[5-(aminoiminomethyl)-2-pyrimidinyl]-1-oxopentyl]amino]-phenylpropanoic acid

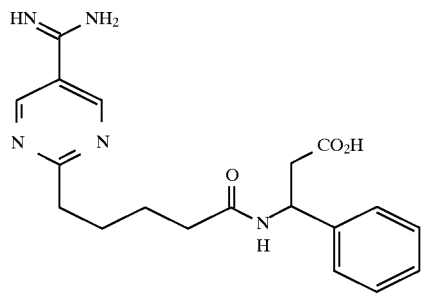

Step 1. Preparation of ethyl 6-amino-6-imino-hexanoate hydrochloride

A mixture of 28 g methyl 5-cyanovalerate, 20 mL ethanol and 100 mL of 4N HCl in dioxane were mixed in a flask under a dry nitrogen atmosphere. The resulting solution was stirred at 40° C. for 36 hr in the stoppered flask. Diethyl ether (1 L) was added to the mixture and the mixture concentrated under a flow of nitrogen until an oily residue was obtained. The residue was triturated with 1 L of hexane and the supernatant liquid was decanted. The hexane trituration procedure was repeated twice until a waxy solid was obtained, which was rapidly isolated by filtration under nitrogen. A solution of ammonia in methanol was added until the reaction mixture was basic and the resulting mixture was stirred at room temperature for 36 hr. The reaction mixture was concentrated in vacuo to a thick oil: $^1$H NMR (DMSO-d6) δ 1.2 (t, J=7.5 Hz, 3H); 1.6 (m, 4H); 2.4 (m, 4H); 4.05 (q, J=7.5 Hz, 2H); 8.8 (bs, 2H); 9.1 (bs, 2H); MS (M+H+ for $C_8H_{16}N_2O_2$) 173.1.

This material usually contained various quantities (up to 30%) of the corresponding methyl ester. No attempts were made to separate the two esters and the mixture was used as such in the next step.

Step 2. Preparation of ethyl 5-cyano-2-pyrmidinepentanoate

A mixture of the amidine from Step 1 (30 g), 15 g of 2-cyano-3-(N,N-dimethylamino)acrolein (C. Reichart and W-D Kermer, Synthesis 1970, 2, 538). 75 mL pyridine and 75 mL triethylamine was stirred at 80° C. for 5 hr. The reaction mixture was concentrated in vacuo and partitioned between diethyl ether and water (pH 4). Concentration of the dried diethyl ether phase provided 20 g of a brown oil, which was purified by silica gel chromatography (eluant hexane-:ethyl acetate 1:1). The pyrimidine derivative was obtained as a 2:1 mixture of the methyl and ethyl esters (12 g): $^1$H NMR (DMSO-d6) δ 1.25 (t, J=7.5 Hz); 1.65 (m, 2H); 1.85 (m, 2H); 2.35 (m, 2H); 3.05 (m, 2H); 3.65 (s); 4.1 (q, J=7.5 Hz); 8.9 (s, 2H).

Step 3. Preparation of 5-cyano-2-pyrimidinepentanoic acid

The esters mixture from Step 2 was stirred at 25° C. with 50 mL 2N hydrochloric acid. After 36 hr reaction, a yellow precipitate had formed which was filtered, washed with some water to give a waxy material which was dried in vacuo to yield a yellow solid (7 g): mp 99.0° C.; $^1$H NMR (DMSO-d6) δ 1.54 (m, 2H); 1.77 (m, 2H); 2.25 (m, 2H); 2.97 (m, 2H); 9.2 (s, 2H); ME (ES, M+H+) 206; IR 2227 cm$^{-1}$.

Step 4. Preparation of β[[5-[5-cyano-2-pyrimidinyl]-1-oxopentyl]amino]-phenylpropanoic acid In a flask under an inert atmosphere, 280 mg of the 5 nitrile (1.37 mmol) prepared in Step 3 of Example 1 was mixed with 190 μL (1.37 mmol) of isobutylchloroformate and 150 μL NMM (1.4 mmol) in 5 mL dry dimethylformamide. The mixture was stirred for 5 min and 225 mg (1.37 mmol) of 3-amino-3-phenylpropionic acid was added. The mixture was stirred at 25° C. for 16 hr and concentrated in vacuo. The residue was purified by HPLC and obtained as a white powder: $^1$H NMR (DMSO-d6) δ 1.8 (m, 4H); 2.3 (m, 2H); 2.9 (d, J=6.8 Hz, 2H) 3.05 (t, J=6 Hz, 2H); 4.35 (m, 1H); 5.5 (dd, J=6.8 and 9 Hz, 1H); 6.72 (d, J 9 Hz, 1H); 7.35 (m, 5H); 8.9 (s, 2H).

Step 5—Preparation of β[[5-[5-(aminoiminomethyl)-2-pyrimidinyl]-1-oxopentyl]amino]-phenylpropanoic acid The material (230 mg) isolated in Step 1 was stirred in 10 mL 10% ammonia in methanol at 25° C. for 26 hr. A new peak was identified and separated by HPLC. After lyophilization to remove eluent, a white powder (26 mg) was isolated: $^1$H NMR (DMSO-d6) δ 1.5 (m, 2H); 1.72 (m, 2H);

2.1 (m, 2H); 2.6 (m, 2H); 2.95 (m, 2H); 4.5 (m, 1H); 7.2 (m, 5H); 8.45 (d, J=8 Hz, 1H); 9.05 (s, 2H); 9.2 (bs, 2H); 9.6 (bs, 2H); MS (M+H+) 370.2.

EXAMPLE 4

N-[5-[5-(aminoiminomethyl)-2-pyrimidinyl]-1-oxopentyl]-β-alanine

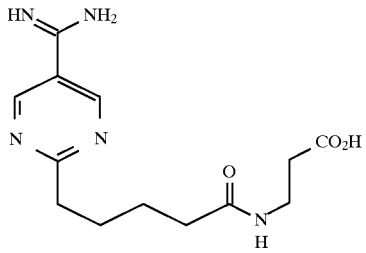

Step 1—Preparation of tert-butyl N-[5-[5-cyano-2-pyrimidinyl]-1-oxopentyl]-β-alaninate In a flask under an inert atmosphere, 1.05 g of the nitrile (5 mmol) prepared in Step 3 of Example 1 was mixed with 750 μL (5.5 mmol) of isobutylchloroformate and 600 μL NMM (5 mmol) in 20 mL dry dimethylformamide. The mixture was stirred for 2 min and 5.5 mmol (1 g) of β-alanine t-butyl ester hydrochloride in 10 mL DMF and 600 μL NMM were added. The mixture was stirred at 25° C. for 16 hr and concentrated in vacuo. The residue was purified by HPLC. The title compound (350 mg) was obtained as a white powder: $^1$H NMR (DMSO-d6) δ 1.4 (s, 9H); 1.7 (m, 2H); 1.9 (m, 2H); 2.2 (m, 2H); 2.45 (m, 2H); 3 (m, 2H); 3.5 (m, 2H); 6.25 (bs, 1H); 8.9 (s, 2H).

Step 2—Preparation of N-[5-[5-(aminoiminomethyl)-2-pyrimidinyl]-1-oxopentyl]-β-alanine The material collected in Step 1 of Example 4 was dissolved in a mixture of 5 mL TFA and 5 mL dichloromethane. The reaction was allowed to stir under a flow of nitrogen at 25° C. for 16 hr at room temperature. After complete removal of the solvents in vacuo, the resulting material was dissolved in 10 mL of methanol saturated with ammonia. The mixture was allowed to stir in an enclosed vial for 3 days at room temperature. The solvents were removed in vacuo and the resulting glass was purified by reverse-phase HPLC (RPHPLC). The title compound was obtained as a hygroscopic white solid: $^1$H NMR (DMSO-d6) δ 1.45 (m, 2H); 1.7 (m, 2H); 2.05 (m, 2H); 2.32 (m, 2H); 2.95 (m, 2H); 3.2 (m, 2H); 7.85 (m, 1H); 9.05 (s, 2H); 9.4 (bs, 2H) & 9.5 (bs, 2H); MS (M+H+ for $C_{13}H_{19}N_5O_3$ 294.1.

EXAMPLE 5

Ethyl N-[5-[5-aminoiminomethyl-2-pyrimidinyl]-1-oxopentyl]-β-alaninate

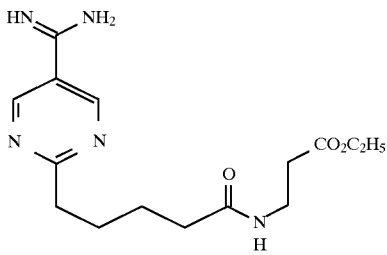

Step 1—Preparation of tert-butyl N-[5-[5-cyano-2-pyrimidinyl]-1-oxopentyl]-β-alaninate The title compound was prepared from 2.7 g of 5-cyano-2-pyrimidinepentanoic acid and 2.7 g β-alanine t-butyl ester using a procedure similar to that described in step 1 of Example 4. The crude material (5 g) obtained after removal of the solvents in vacuo was used without further purification in the next step.

Step 2—Preparation of tert-butyl N-[5-[5-(aminoiminomethyl)-2-pyrimidinyl]-1-oxopentyl]-β-alaninate The material obtained in step 1 of Example 5 was dissolved in 50 mL of methanol saturated with ammonia. The reaction mixture was allowed to stir at 25° C. for 5 days in a sealed vial. After removal of the solvents, the residue was purified by RPHPLC to afford about 2 g of the trifluoroacetic acid salt of the amidine as a yellow glass: MS (M+H+ for $C_{17}H_{26}N_{26}N_5O_3$) 350.2.

Step 3—Preparation of ethyl N-[5-[5-(amino-iminomethyl)-2-pyrimidinyl]-1-oxopentyl]-β-alaninate In a flask under inert atmosphere, were combined 1.5 g of tert-butyl N-[5-[5-(amino-iminomethyl)-2-pyrimidinyl]-1-oxopentyl]-β-alaninate, 100 mL dry ethanol and 10 mL of 4N HCl in dioxane. The mixture was allowed to stir at room temperature for 48 hr. The excess of HCl was blown out with a stream of nitrogen and the solvents removed in vacuo. After purification of the main product by HPLC, a slightly yellow glass was obtained by lyophilization (400 mg): $^1$H NMR (DMSO-d6) δ 1.20 (t, J=7 Hz, 3H); 1.5 (m, 2H); 1.75 (m, 2H); 2.05 (m, 2H); 2.4 (m, 2H); 2.95 (m, 2H); 3.25 (m, 2H); 4.05 (q, J=7 Hz, 2H); 7.95 (m, 1H); 9.05 (s, 2H); 9.5 (bs, 4H).

Elemental Analysis: Calcd for $C_{15}H_{23}O_3N_5 \cdot CF_3CO_2H \cdot 0.7H_2O$. C, 45.57; H, 5.71; N, 15.63; Found: C, 46.04; H, 5.51; N, 15.24.

EXAMPLE 6

β-[[5-[5-(aminoiminomethyl)-2-pyrimidinyl]-1-oxopentyl]amino]-3-pyridinepropanoic acid

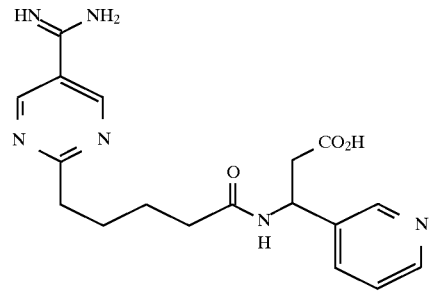

Step 1. Preparation of benzyl β-[[5-[5-(cyano)-2-pyrimidinyl]-1-oxopentyl]amino]-3-pyridinepropanoate In a flask under an inert atmosphere, 0.9 g of the nitrile (4.5 mmol) prepared in step 3 of Example 1 was mixed with 600 μL (4.6 mmol) of isobutylchloroformate and 500 μL NMM (4.6 mmol) in 25 mL dry dimethylformamide. The mixture was stirred for 5 min and 4.56 mmol (1.5 g) of benzyl β-(3-pyridine)propanoate dihydrochloride in 30 mL dimethylformamide and 500 μL NMM were added. The mixture was stirred at 25° C. for 16 hr and concentrated in vacuo. The residue was purified by silica gel chromatography (methanol:chloroform, 5:95 as eluant). he title compound (2 g) was obtained as a yellow oil.

Step 2. Preparation of β-[[5-[5-(cyano)-2-pyrimidinyl]-1-oxopentyl]amino]-3-pyridinepropanoic acid A portion of the material isolated in Step 1 of Example 6 (1 g) was stirred in a mixture of ethanol and 2N hydrochloric acid for 16 hr at 25° C. The solvents were removed in vacuo and the remaining viscous oil was identified as the desired product; FABMS (M+H+ for $C_{18}H_{19}N_5O_3$) 354.1.

Step 3. Preparation of β-[[5-[5-(aminoiminomethyl)-2-pyrimidinyl]-1-oxopentyl]amino]-3-pyridinepropanoic acid β-[[5-[5-(cyano)-2-pyrimidinyl]-1-oxopentyl]amino]-3-pyridinepropanoic acid isolated in the Step 2 above, was dried in vacuo and dissolved in 20 mL methanol saturated with ammonia and allowed to stir at 25° C. for 96 hr (20 more mL methanol saturated in ammonia was added after 36 hr). The solvents were removed in vacuo and the remaining material purified by RPHPLC. A clear glass (300 mg) was obtained after lyophilization. Part of this material (100 mg) was repurified by RPHPLC to obtain 45 mg of a white solid: $^1$H NMR (CD$_3$OD) δ 1.65 (m, 2H); 1.85 (m, 2H); 2.25 (m, 2H); 2.94 (m, 2H); 3.05 (m, 2H); 5.4 (m, 2h); 7.85 (m, 1H); 8.4 (d, J=8 Hz, 1H); 8.6 (d, J=6 Hz, 1H); 9.05 (s, 2H); FAMBS (M+H+ for $C_{18}H_{22}N_6O_3$) 371.2.

Exact Mass: Calcd for $C_{18}H_{22}N_6O_3$ M+H+ 371.1831; Found: 371.1859.

EXAMPLE 7

β-[[5-[5-(aminoiminomethyl)-2-pyrimidinyl]-1=oxopentyl]amino]-amino-1,3-benzodioxole-5-propanoic acid

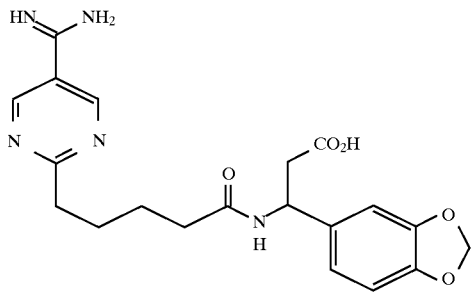

Step 1. Ethyl β-amino-1,3-benzodioxole-5-propanoate.HCl 3,4-Methylenedioxybenzaldehyde (6.0 g; 40 mmoles), malonic acid (5.2 g; 50 mmoles) and ammonium acetate (4 g; 52 mmoles) were gently refluxed in ethanol (350 ml) overnight. The reaction mixture was allowed to cool down to room temperature and the solid precipitate was collected by filtration and washed with ethanol/water (1:1; 2×100 ml). The air-dried free acid (3 g) [FAVMS; MH+210] was suspended in absolute ethanol (200 ml). The solution was cooled in an ice bath and treated with dried HCl gas for 1 h. The reaction mixture was stirred at room temperature overnight and the solvent was removed on a rotary evaporator. The residue was dried in vacuum dessicator to give 3.2 g of ester [FABMS:MH+=238]. This material was used without any further purification.

Step 2.—Preparation of ethyl β-[[5-[5-(cyano)-2-pyrimidinyl]-1-oxopentyl]amino]-amino-1,3-benzodioxole-5-propanoate.

In a flask under an inert atmosphere, 0.8 g of the nitrile (4 mmol prepared in Step 3 of Example 1 was mixed with 600 μL of (4.5 mmol) of isobutylchloroformate and 1 mL NMM (9 mmol) in 25 mL dry dimethylformamide. The mixture was stirred for 5 min and 4.5 mmol (1.1 g) of ethyl β-amino-1,3-benzodioxole-5-propanoate hydrochloride in 10 mL dimethylformamide and 500 μL NMM were added. The mixture was stirred at 25° C. for 16 hr and concentrated in vacuo. The residue was partitioned between ethyl acetate and water. After drying and removing the solvents in vacuo, the title compound was obtained as a yellow oil (1.05 g).

Step 3. Preparation of β-[[5-[5-(cyano)-2-pyrimidinyl]-1-oxopentyl]amino]-amino-1,3-benzodioxole-5-propanoate A portion of the material isolated in Step 1 of Example 6 (1 g) was stirred in a mixture of ethanol and 2N hydrochloric acid for 16 hr at 25° C. The solvents were removed in vacuo and the remaining viscous oil was identified as the desired product by proton NMR.

Step 4. Preparation of β-[[5-[5-(aminoiminomethyl)-2-pyrimidinyl]-1-oxopentyl]amino]-amino-1,3-benzodioxole-5-propanoate The β-[[5-[5-(cyano)-2-pyrimidinyl]-1-oxopentyl]amino]-β-amino-1,3-benzodioxole-5-propanoate isolated in the Step 3 above, was dried in vacuo and dissolved in 20 mL of methanol saturated with ammonia, and allowed to stir at 25° C. for 96 hr (an additional 20 mL of methanol saturated in ammonia were added after 36 hr). The solvents were removed in vacuo and the remaining material purified by RPHPLC and the desired fraction lyophilized to a slightly yellow powder: $^1$H NMR (DMSO-d6) δ 1.75 (m, 2H); 2.05 (m, 2H); 2.20 (t, 2H, J=7.5 Hz); 2.94 (m, 2H); 3.05 (t, 2H, J=7.5 Hz); 5.4 (m, 1H); 6.25 (s, 2H); 7.1 (m, 3H); 8.55 (d, J—8 Hz, 1H); 8.6 (d, J=6 Hz, 1H); 9.35 (s, 2H); 9.5 (bs, 2H); 9.8 (bs, 2H); FABMS (M+H+ for $C_{20}H_{23}N_5O_5$) 414.

Elemental Analysis: Calcd for $C_{20}H_{23}N_5O_5 \cdot H_2O$. C, 48.44; H, 4.80; N, 12.83; Found: C, 48.75; H, 4.56; N, 12.68.

Inhibition of Platelet Aggregation

The compounds of this invention are particularly useful for the inhibition of platelet aggregation and treatment of indications requiring inhibition or modulation of platelet aggregation.

In-Vitro Platelet Aggregation in PRP

Healthy male or female dogs were fasted for 8 hours prior to drawing blood; then 30 mL whole blood was collected using a butterfly needle and 30 mL plastic syringe with 3 mL of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature allowing the centrifuge to coast to a stop without braking. The PRP was removed from the blood with a plastic pipette and placed in a plastic-capped 50 mL Corning conical sterile centrifuge tube which was held at room temperature. Platelet-poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets/mL. The PRP preparation (400 μL) and 50 μL of the compound solution to be tested or saline were preincubated for 1 minute at 37° C. in a BioData aggregometer (BioData, Horsham, Pa.). Adenosine-5'-diphosphate (ADP, 50 μL, 50 μM final concentration) was added to the cuvettes and the aggregation was monitored for 1 minute. All compounds are tested in duplicate. Results are calculated as follows: Percent of control=[(maximal OD minus initial OD of compound) divided by (maximal OD minus initial OD of control saline) ]×100. The percent inhibition equals 100-(percent of control).

The compounds tested and their median inhibitory concentrations (IC$_{50}$) are recorded in Table 1. The IC$_{50}$ (dosage at which 50% of platelet aggregation is inhibited) were calculated by linear regression of the dose response curve. The assay results for the compounds of Examples 1 to 14 are also set forth in Table 1.

Inhibition of Ex Vivo Collagen-Induced Aggregation

The purpose of this assay is to determine the effects of antiplatelet compounds on ex vivo collagen-induced platelet aggregation when administered either intravenously or orally to dogs.

Pretreatment (control) blood samples are drawn from either conscious or anesthetized dogs (Beagles) and centrifuged to prepare platelet-rich plasma (PRP). Aggregatory response to collagen is measured in an aggregometer and used as a control. Compounds are administered, either intragastrically (either by capsule or stomach tube) or intravenously. Blood samples are drawn at predetermined intervals after compound administration, PRP is prepared and aggregation to collagen determined. Compound inhibition of aggregation is determined by comparing the aggregation response after compound administration to the pretreatment response.

TABLE 1

BIOLOGICAL DATA

|  | $IC_{50}$ | Ex Vivo Effect |
|---|---|---|
| Ex. 1 | 5.9 e-07 | NT |
| Ex. 2 | 1.1 e-07 | NT |
| Ex. 3 | 2.2 e-06 | NT |
| Ex. 4 | 5.0 e-05 | NT |
| Ex. 5 | NT | + |
| Ex. 6 | 5.3 e-07 | NT |
| Ex. 7 | NT |  |

Other variations and modifications of this invention will be obvious to those skilled in the art. This invention is not limited except as set forth in the claims.

What is claimed is:

1. A compound having the formula:

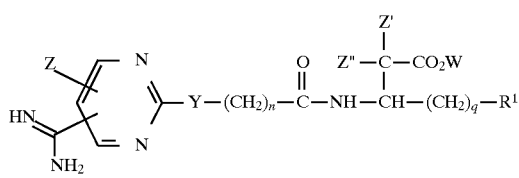

or a pharmaceutically acceptable salt thereof, wherein

Z, Z', and Z" are independently halo, alkoxy, alkyl, hydrogen or hydroxy;

Y is methylene, alkenyl having 2 to 4 carbon atoms, alkynyl having 2 to 4 carbon atoms or carbonyl;

n is an integer from 1 to 6;

W is hydrogen, alkyl, methoxyalkyl or aralkyl;

q is an integer from 0 to 3; and $R^1$ is hydrogen; alkyl; cycloalkyl; alkoxy; alkylthio; alkylsulfonyl; aryl; aralkyl; heterocyclic; or

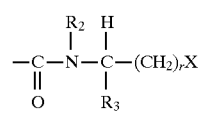

wherein $R^2$ is hydrogen, alkyl, aryl, or aralkyl;

$R^3$ is hydrogen, alkyl, aryl, or aralkyl;

r is an integer from 0 to 2; and

X is CN, $CO_2R^4$, $CONH_2$, $CONHR^4$ or $CON(R^4)_2$; wherein $R^4$ is hydrogen, alkyl, aryl, or aralkyl.

2. The compound of claim 1, wherein Z, Z', and Z" are hydrogen.

3. The compound of claim 2, wherein q is 0, and Y is methylene.

4. The compound of claim 3, wherein n is 3, and $R^2$ is hydrogen.

5. The compound of claim 4, wherein r is 0.

6. A compound according to claim 1, which is [$S$,($R*$, $R*$)]-3-[[5-[5-(aminoiminomethyl)-2-pyrimidinyl]-1-oxopentyl]amino]-4-[[2-amino-2-oxo-1-(phenylmethyl)ethyl]amino]-4-oxobutanoic acid.

7. A compound according to claim 1, which is N-[N-[-[5-(aminoiminomethyl)-2-pyrimidinyl]-1-oxopentyl]-L-alpha-aspartyl-L-phenylalanine.

8. A compound according to claim 1, which is β-[[5-[5-(aminoiminomethyl)-2-pyrimidinyl]-1-oxopentyl]amino]-phenylpropanoic acid.

9. A compound according to claim 1, which is N-[5-[5-(aminoiminomethyl)-2-pyrimidinyl]-1-oxopentyl]-β-alanine.

10. A compound according to claim 1, which is Ethyl-N-[5-[5-(aminoiminomethyl)-2-pyrimidinyl]-1-oxopentyl]-O-alaninate.

11. A compound according to claim 1, which is β-[[5-[5-(aminoiminomethyl)-2-pyrimidinyl]-1-oxopentyl]amino]-3-pyridinepropanoic acid.

12. A compound according to claim 1, which is β-[[5-[5-(aminoiminomethyl)-2-pyrimidinyl]-1-oxopentyl]amino]-amino-1,3-benzodioxole-5-propanoic acid.

13. A pharmaceutical composition comprising at least one non-toxic pharmaceutically acceptable carrier and at least one compound according to any of claims 1–12.

14. A method of treating a mammal in need of platelet aggregation inhibition treatment comprising administering a therapeutically effective amount of the compound of any of claims 1–12 to the mammal.

* * * * *

UNITED STATES PATENT AND TRADEMARK OFFICE
CERTIFICATE OF CORRECTION

PATENT NO. : 5,872,122

DATED : February 16, 1999

INVENTOR(S) : Philippe R. Bovy et al.

It is certified that error appears in the above-identified patent and that said Letters Patent is hereby corrected as shown below:

COLUMN 1

Line 60, "European" should read --¶European--.

COLUMN 5

Line 48, "sucrose" should read --sucrose,--.
   Line 60, "agents" should read --agents,--.

COLUMN 6

Line 26, "Press;," should read --Press,-- and "York))," should read --York),--.

COLUMN 18

Line 27, "538)." should read --538),--.
   Line 49, "5" should be deleted.

UNITED STATES PATENT AND TRADEMARK OFFICE
CERTIFICATE OF CORRECTION

PATENT NO. : 5,872,122

DATED : February 16, 1999

INVENTOR(S) : Philippe R. Bovy et al.

It is certified that error appears in the above-identified patent and that said Letters Patent is hereby corrected as shown below:

COLUMN 19

Line 49, "C.H..N.O.294.1." should read --$C_{13}H_{19}N_5O_3$) 294.1.--.

COLUMN 20

Line 64, "he" should read --The--.

COLUMN 21

Line 27, "1=oxopentyl]" should read --1-oxopentyl]--.

COLUMN 22

Line 23, "J-8" should read --J=8--.

UNITED STATES PATENT AND TRADEMARK OFFICE
CERTIFICATE OF CORRECTION

PATENT NO.   :   5,872,122

DATED        :   February 16, 1999

INVENTOR(S)  :   Philippe R. Bovy et al.

It is certified that error appears in the above-identified patent and that said Letters Patent is hereby corrected as shown below:

<u>COLUMN 24</u>

Line 25, "[5-" should read --[5-[5- --.

Signed and Sealed this

Thirtieth Day of November, 1999

Attest:

Q. TODD DICKINSON

Attesting Officer

Acting Commissioner of Patents and Trademarks